US011844639B2

(12) United States Patent
Fan et al.

(10) Patent No.: US 11,844,639 B2
(45) Date of Patent: Dec. 19, 2023

(54) SYSTEM AND METHOD FOR UTILIZING DUAL ENERGY IMAGING IN A COMPUTED TOMOGRAPHY IMAGING SYSTEM

(71) Applicant: GE PRECISION HEALTHCARE LLC, Wauwatosa, WI (US)

(72) Inventors: Jiahua Fan, New Berlin, WI (US); Ming Yan, Hartland, WI (US); Jed Douglas Pack, Glenville, WI (US); Priti Madhav, Brookfield, WI (US); Kentaro Ogata, Hachioji (JP); Ken Arai, Setagaya (JP)

(73) Assignee: GE Precision Healthcare LLC, Wauwatosa, WI (US)

( * ) Notice: Subject to any disclaimer, the term of this patent is extended or adjusted under 35 U.S.C. 154(b) by 237 days.

(21) Appl. No.: 17/514,201

(22) Filed: Oct. 29, 2021

(65) Prior Publication Data

US 2023/0138814 A1 May 4, 2023

(51) Int. Cl.
*A61B 6/00* (2006.01)
*A61B 6/03* (2006.01)
*G06N 3/02* (2006.01)

(52) U.S. Cl.
CPC .............. *A61B 6/482* (2013.01); *A61B 6/032* (2013.01); *A61B 6/5205* (2013.01); *G06N 3/02* (2013.01)

(58) Field of Classification Search
CPC ....... A61B 6/482; A61B 6/032; A61B 6/5205; A61B 6/4007; A61B 6/4014; A61B 6/486;

(Continued)

(56) References Cited

U.S. PATENT DOCUMENTS 9,247,919 B2 * 2/2016 Goshen .................. A61B 6/52
9,274,066 B2   3/2016 Ji et al.
(Continued)

FOREIGN PATENT DOCUMENTS

JP   2009082173 A   4/2009
JP   2009279289 A   12/2009
(Continued)

OTHER PUBLICATIONS

Cuadros Angela P et al: "Low-Dose Dual KVP Switching Using a Static Coded Aperture", 2021 IEEE 18th International Symposium on Biomedical Imaging (ISBI), IEEE, Apr. 13, 2021 (Apr. 13, 2021), pp. 1057-1061, XP033917878, DOI: 10.1109/ISBI48211. 2021.9434080 [retrieved on May 17, 2021].

(Continued)

*Primary Examiner* — Courtney D Thomas
(74) *Attorney, Agent, or Firm* — Fletcher Yoder P.C.

(57) ABSTRACT

A method includes acquiring a first dataset of projection measurements at a first energy spectrum and a second dataset of projection measurements at a second energy spectrum different from the first energy spectrum by switching between acquiring the first dataset for a set number of consecutive views at different projection angles at the first energy spectrum and acquiring the second dataset for the set number of consecutive views at different projection angles at the second energy spectrum. The set number of consecutive views is greater than one. The method includes supplementing both the first dataset with estimated projection measurements at the first energy spectrum and the second dataset with estimated projection measurements at the second energy spectrum to provide missing projection measurements at different projection angles not acquired during the imaging scan for the first dataset and the second dataset.

20 Claims, 4 Drawing Sheets

(58) Field of Classification Search
CPC ......... A61B 6/02; A61B 6/405; A61B 6/4241; A61B 6/5258; G06N 3/02; G06T 11/006; G06T 2211/408; G01N 2223/206; G01N 2223/306; G01N 2223/316; G01N 2223/3304; G01N 2223/419; G01N 2223/423; G01N 23/046; G01N 23/087
See application file for complete search history.

(56) References Cited

U.S. PATENT DOCUMENTS

| | | |
|---|---|---|
| 9,498,178 B2 | 11/2016 | Ji et al. |
| 2011/0052022 A1 | 3/2011 | Xu |
| 2014/0086383 A1 | 3/2014 | Huwer |
| 2018/0182129 A1 | 6/2018 | Xing |
| 2021/0007691 A1 | 1/2021 | Prabhu Verleker |

FOREIGN PATENT DOCUMENTS

| | | |
|---|---|---|
| JP | 2010131215 A | 6/2010 |
| WO | 2023003924 A1 | 1/2023 |

OTHER PUBLICATIONS

EP patent application 22201479.7 filed Oct. 13, 2022—extended Search Report dated Mar. 9, 2023; 11 pages.
JP2009082173_English_Abstract_Espacenet_searchresults_Jun. 6, 2023.
JP2009279289_English_Abstract_Espacenet_searchresults_Jun. 6, 2023.
JP2010131215_English_Abstract_Espacenet_searchresults_Jun. 6, 2023; 1 page.
Almeida, Isabel P., et al.; "Dual-energy CT quantitative imaging: a comparison study between twin-beam and dual-source CT scanners"; Med. Phys. 44(1); Jan. 2017; pp. 171-179.

* cited by examiner

SYSTEM AND METHOD FOR UTILIZING DUAL ENERGY IMAGING IN A COMPUTED TOMOGRAPHY IMAGING SYSTEM

BACKGROUND

The subject matter disclosed herein relates to digital X-ray systems and, more particularly, to techniques for utilizing dual energy computed tomography imaging.

Non-invasive imaging technologies allow images of the internal structures or features of a subject (patient, manufactured good, baggage, package, or passenger) to be obtained non-invasively. In particular, such non-invasive imaging technologies rely on various physical principles, such as the differential transmission of X-rays through the target volume or the reflection of acoustic waves, to acquire data and to construct images or otherwise represent the internal features of the subject.

For example, in X-ray-based imaging technologies, X-ray radiation spans a subject of interest, such as a human patient, and a portion of the radiation impacts a detector where the intensity data is collected. In digital X-ray systems, a detector produces signals representative of the amount or intensity of radiation impacting discrete pixel regions of a detector surface. The signals may then be processed to generate an image that may be displayed for review.

In one such X-ray based technique, known as computed tomography (CT), a scanner may project fan-shaped or cone-shaped X-ray beams from an X-ray source at numerous view angle positions about an object being imaged, such as a patient. The X-ray beams are attenuated as they traverse the object and are detected by a set of detector elements which produce signals representing the intensity of the incident X-ray intensity on the detector. The signals are processed to produce data representing the line integrals of the linear attenuation coefficients of the object along the X-ray paths. These signals are typically called "projection data" or just "projections". By using reconstruction techniques, such as filtered backprojection, images may be generated that represent a volume or a volumetric rendering of a region of interest of the patient or imaged object. In a medical context, pathologies or other structures of interest may then be located or identified from the reconstructed images or rendered volume.

Dual energy CT imaging (e.g., spectral CT imaging) involves acquiring CT datasets at two different X-ray energy-spectra and performing multi-material decomposition on those datasets to obtain two or more material images (e.g., material decomposition images or basis material images) representative of multiple materials (water, iodine, calcium, etc.). The primary hardware solutions for dual energy imaging include fast kVp switching, split filter, dual X-ray sources, and dual layer detectors. However, the utilization of this hardware makes the CT imaging system more expensive. Low-end CT imaging systems (which lack the above hardware solutions for dual energy imaging) consist of cost effective hardware and only have slower kVp switching capability. In addition, the detector of the low-end CT imaging systems may utilize a cheaper scintillator material that includes properties (e.g., slower primary speed and higher afterglow) that make it undesirable and difficult to achieve acceptable imaging quality and material quantification in dual energy images scanned with fast kVp switching. Due to the clinical value of dual energy imaging, many CT users are converting their standard protocols to use dual energy for a vast number of clinical applications (e.g., kidney stones, lesion characterization, bone edema, etc.). It would be desirable to provide dual energy capability to the low-end CT imaging systems.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a computer-implemented method is provided. The method includes acquiring, during an imaging scan, a first dataset of projection measurements at a first energy spectrum and a second dataset of projection measurements at a second energy spectrum different from the first energy spectrum by switching between acquiring the first dataset for a set number of consecutive views at different projection angles at the first energy spectrum and acquiring the second dataset for the set number of consecutive views at different projection angles at the second energy spectrum, wherein the set number of consecutive views is greater than one. The method also includes supplementing both the first dataset with estimated projection measurements at the first energy and the second dataset with estimated projection measurements at the second energy spectrum to provide missing projection measurements at different projection angles not acquired during the imaging scan for the first dataset and the second dataset respectively.

In another embodiment, one or more non-transitory computer-readable media is provided. The one or more non-transitory computer-readable media encode one or more processor-executable routines, wherein the one or more routines, when executed by a processor, cause acts to be performed. The acts include acquiring, during an imaging scan, a first dataset of projection measurements at a first energy spectrum and a second dataset of projection measurements at a second energy spectrum different from the first energy spectrum by switching between acquiring the first dataset for a set number of consecutive views at different projection angles at the first energy spectrum and acquiring the second dataset for the set number of consecutive views at different projection angles at the second energy spectrum, wherein the set number of consecutive views is greater than one. The acts also include supplementing both the first dataset with estimated projection measurements at the first energy spectrum and the second dataset with estimated projection measurements at the second energy spectrum to provide missing projection measurements at different projection angles not acquired during the imaging scan for the first dataset and the second dataset respectively.

In a further embodiment, a processor-based system is provided. The system includes a memory encoding processor-executable routines. The system also includes a processor configured to access the memory and to execute the processor-executable routines, wherein the routines, when executed by the processor, cause the processor to perform acts. The acts include acquiring, during an imaging scan, a first dataset of projection measurements at a first energy spectrum and a second dataset of projection measurements at a second energy spectrum different from the first energy spectrum by switching between acquiring the first dataset for a set number of consecutive views at different projection angles at the first energy spectrum and acquiring the second dataset for the set number of consecutive views at different projection angles at the second energy spectrum, wherein the set number of consecutive views is greater than one. The acts also include supplementing both the first dataset with estimated projection measurements at the first energy spectrum and the second dataset with estimated projection measurements at the second energy spectrum to provide missing projection measurements at different projection angles not acquired during the imaging scan for the first dataset and the second dataset respectively.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications). In general, the present approaches may be desirable in any imaging or screening context in which a photon-counting detector is utilized.

The present disclosure provides for methods and systems to enable the utilization of kVp switching technology for dual energy imaging on low-end CT imaging systems (which lack typical hardware solutions for dual energy imaging) that consist of cost effective hardware and only have slower kVp switching capability. In particular, the detector response in low-end CT imaging systems is slow and cannot respond fast enough for view by view kVp switching. The disclosed techniques enable the dual energy imaging via kVp switching by switching the tube voltage between high and low energy every n views (where n is greater than one) to provide the detector adequate time to respond to voltage changes. The value of the n and the total number of views per rotation is configured to ensure the high and low kVp measurements (e.g., projection measurements) are interlaced and each one of them has equivalent data. The high and low kVp measurements are then supplemented with estimated projection measurements for the missing projection measurements at different projection angles not acquired during the imaging scans. The estimated projection measurements for the high and low kVp measurements are derived from the low and/or high kVp measurements that correspond to the different projection angles for the missing projection measurements. The supplemented high and low kVp measurements may then be subjected to projection space or image space decomposition and analysis can be applied for dual energy purposes. The disclosed embodiments enable the dual energy imaging via kVp switching via updated software (e.g., algorithm) without having to upgrade the hardware.

Figure 1:
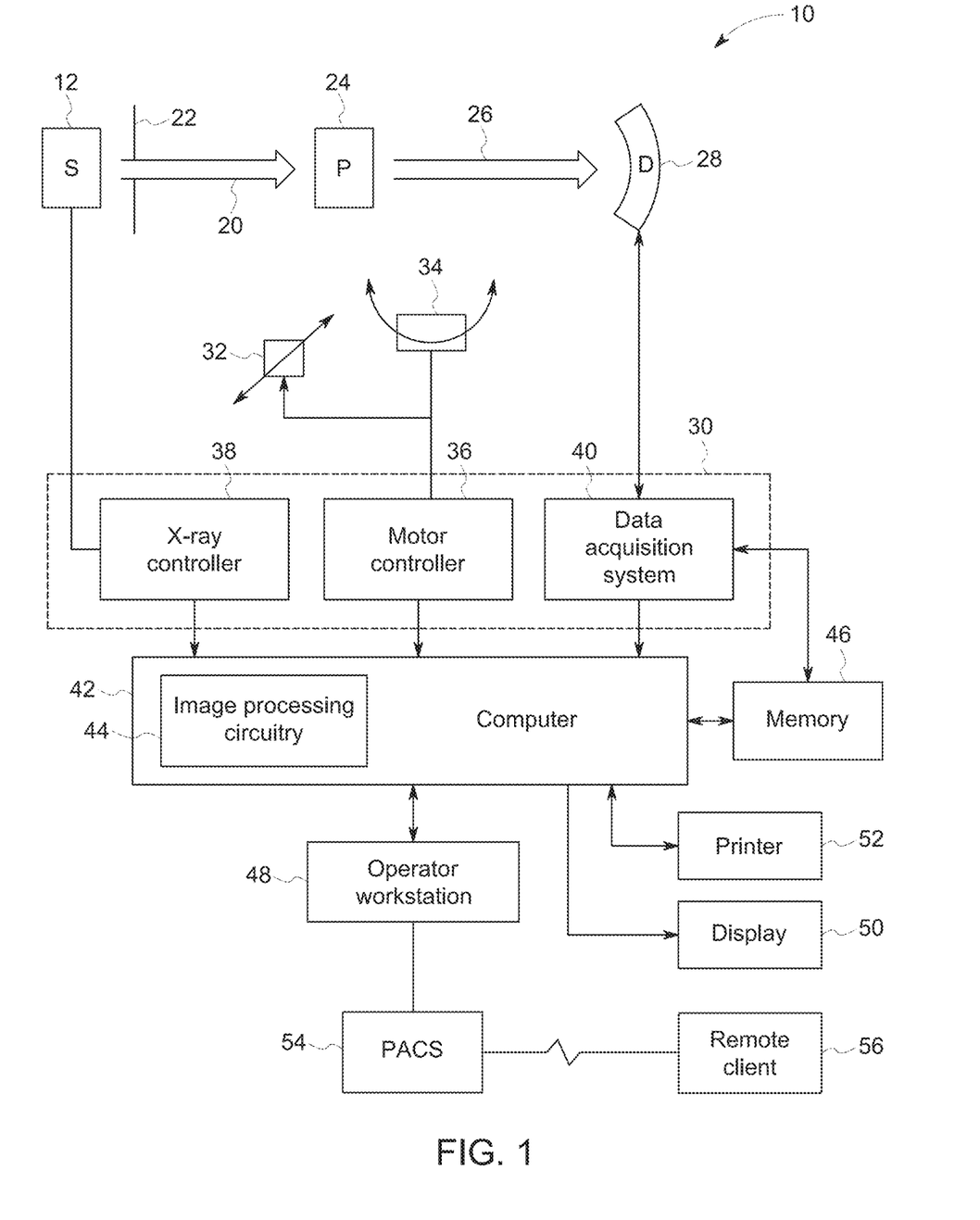
FIG. 1 is a schematic illustration of an embodiment of a computed tomography (CT) system configured to acquire CT images of a patient and process the images, in accordance with aspects of the present disclosure.

With the foregoing discussion in mind, FIG. 1 illustrates an embodiment of an imaging system 10 for acquiring and processing image data in accordance with aspects of the present disclosure. In the illustrated embodiment, system 10 is a computed tomography (CT) system designed to acquire X-ray projection data, to reconstruct the projection data into a tomographic image, and to process the image data for display and analysis. The CT imaging system 10 includes an X-ray source 12. As discussed in detail herein, the source 12 includes a single X-ray source, such as an X-ray tube or solid-state emission structure. The X-ray source 12, in accordance with present embodiments, is configured to emit an X-ray beam 20 at one or more energies. For example, the X-ray source 12 may be configured to switch between relatively low energy polychromatic emission spectra (e.g., at about 80 kVp) and relatively high energy polychromatic emission spectra (e.g., at about 140 kVp). The terms "high" and "low" as utilized herein are relative, with high energy meaning an energy higher than another energy and low energy meaning an energy lower than another energy. As will be appreciated, the X-ray source 12 may also be operated so as to emit X-rays at more than two different energies, though dual-energy embodiments are discussed herein to simplify explanation. Similarly, the X-ray source 12 may emit at polychromatic spectra localized around energy levels other than those listed herein. Indeed, selection of the respective energy levels for emission may be based, at least in part, on the anatomy being imaged and the chemical or molecules of interest for tissue characterization.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector or detector array 28 formed by a plurality of detector elements. The system 10 includes a single detector 28. Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 (e.g., gantry, table, etc.) and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In certain embodiments, the X-ray controller 38 may be configured to provide kVp switching of the X-ray source 12 so as to switch the source 12 to emit X-rays at the respective polychromatic energy spectra in succession (after a set number of views at different angles are acquired for each polychromatic energy spectra) during an image acquisition session. For example, in a dual-energy imaging context, the X-ray controller 38 may operate the X-ray source 12 so that the X-ray source 12 alternately emits X-rays at the two polychromatic energy spectra of interest for a set number of views at each polychromatic energy spectra, such that adjacent sets of projections for a set number of views are acquired at different energies in an alternating manner (i.e., a first set of projections over n views (where N is greater than one) at different angles is acquired at high energy, the second set projection of projections over n views is acquired at low energy, and so forth). In one such implementation, the kVp switching operation performed by the X-ray controller 38 yields temporally registered projection data. The data collection may occur during slow-switching helical scans (e.g., low pitch helical scan) or axial scans (e.g., during rotate-rotate mode). In the rotate-rotate mode, the patient table remains stationary while two energy scans are collected sequentially. This can be either two half-scans (e.g., when utilizing half-scan reconstruction) or two full-scans (e.g., two full rotations). In the slow-switching helical scans, low-pitch helical (e.g., 0.5:1 pitch) is used and the X-ray spectrum is changed either over a half-scan range (180 degree plus fan-angle) or full-scan range (360 degree), or somewhere in between.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include processing circuitry 44 (e.g., image processing circuitry). The computer 42 may include or communicate with one or more non-transitory memory devices 46 that can store data processed by the computer 42, data to be processed by the computer 42, or instructions to be executed by a processor (e.g., processing circuitry 44) of the computer 42. For example, the processing circuitry 44 of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein.

The CT imaging system 10 is a low-end CT imaging system. In particular, the CT imaging system 10 lacks the hardware for dual energy imaging (e.g., fast kVp switching, dual X-ray sources, and dual layer detectors). In addition, the detector 28 of the low-end CT imaging system 10 may utilize a cheaper scintillator material that includes properties (e.g., slower primary speed and higher afterglow) that make it undesirable and difficult to achieve acceptable imaging quality and material quantification in dual energy images scanned with fast kVp switching. As discussed below, the memory 46 may also store instructions (e.g., one or more algorithms) to enable utilization of dual energy imaging with the CT imaging system. For example, the memory 47 enables the acquisition of projection measurements at two different energy levels or spectrums (e.g., high and low kVp) by switching between acquiring a first dataset for a set number of consecutive views at different projection angles at a first energy spectrum and acquiring a second dataset for the set number of consecutive views at different projection angles at a second energy spectrum, wherein the set number of consecutive views is greater than one. The memory 47 enables supplementing both the first dataset with estimated projection measurements at the first energy spectrum and the second dataset with estimated projection measurements at the second energy spectrum to provide missing projection measurements at different projection angles not acquired during the imaging scan for the first dataset and the second dataset respectively.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
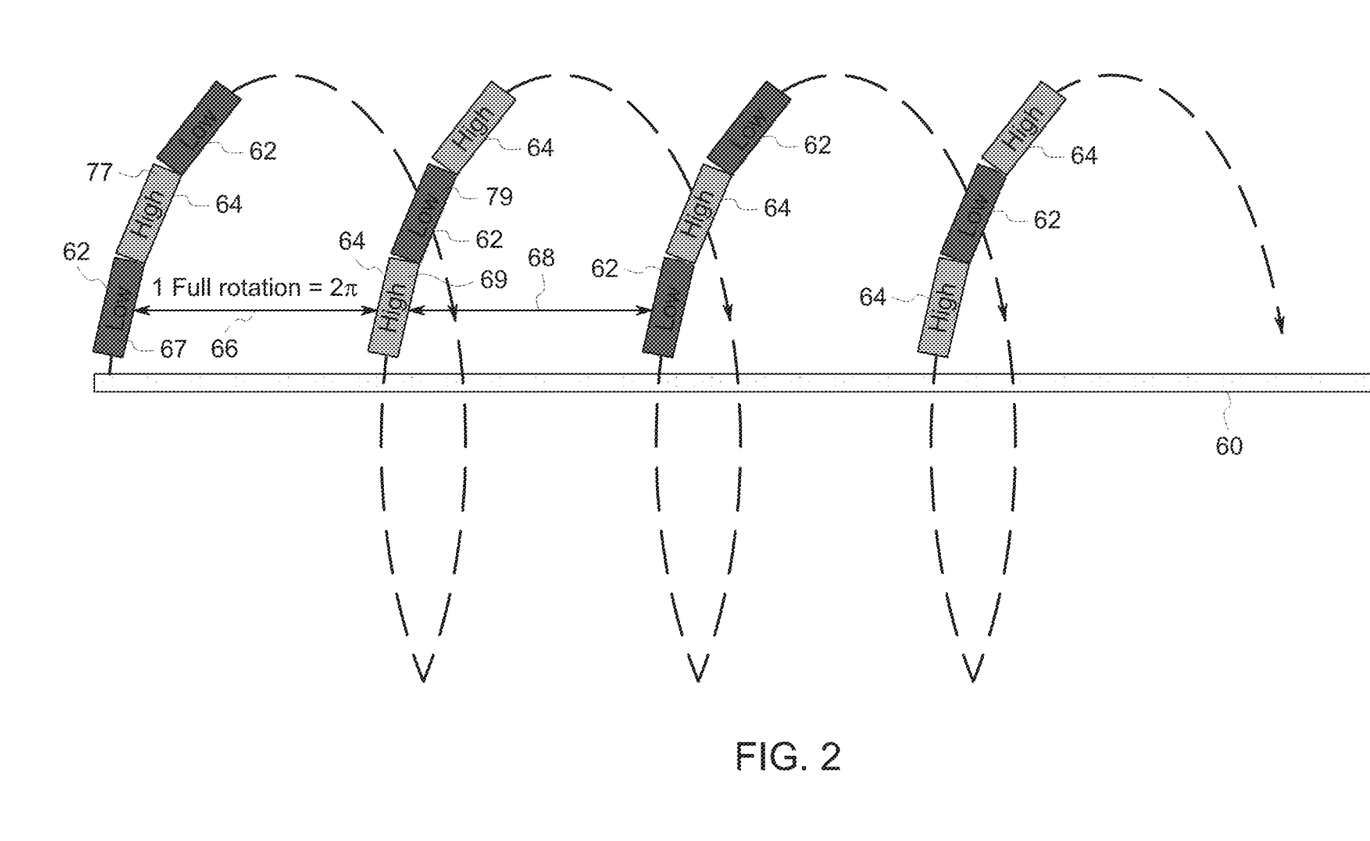
FIG. 2 is a schematic illustration of an embodiment of a kVp switching approach (e.g., for a low pitch helical scan), in accordance with aspects of the present disclosure.

FIG. 2 is a schematic illustration of an embodiment of a kVp switching approach (e.g., for a low pitch helical scan). In the depicted kVp switching approach, where switching is done every nth (n>1) view, the tube voltage changes every nth view and remains constant for the next n views. To form sufficient views for high and low kVp reconstruction, the missing high and low kVp views need to be estimated by algorithms.

Assuming the tube kVp switches every n views and there are m views per rotation, m and n need to satisfy the following requirement:

$$m = 2kn + n, \text{ where } k \text{ is a non-negative integer.} \quad (1)$$

The first view of the high (or low) kVp measurement will be at the starting angle, $\beta_0$. Then, for each following view, the tube rotates $$\Delta \beta = \frac{2\pi}{2kn + n}.$$

After every nth view, the kVp switches from high to low or low to high. After one full rotation is completed, the tube will switch to low (or high) kVp at angle $\beta_0$ (i.e., opposite kVp from the first rotation). In this way, the high and low kVp views will each be able to form one $2\pi$ sampling (e.g., one full rotation) from a $4\pi$ span (e.g., two full rotations). In certain embodiments, the number of rotations for acquiring data may be different (e.g., 4 rotations, 6 rotations, etc.). The actual number of rotations of data acquired for a helical scan will be determined by the z extent that needs to be covered. As depicted in FIG. 2, a helical path 58 for the scan (e.g., low pitch helical scan) is depicted about a table 60 (without the imaged patient present). During the helical scan, the table 60 moves at a constant speed. Sets of n views of projection measurements at low and high kVp gathered at different projection angles along the helical path 58 are represented by reference numerals 62 and 64, respectively. As depicted, a first full rotation 66 begins with a set of low kVp measurements 62 at n views, while the second full rotation 68 begins with a set of high kVp measurements 62 at n views. The sets of low kVp measurements 62 in the first rotation 66 correspond in projection angles with the sets of high kVp measurements 64 in the second rotation 68, while the sets of high kVp measurements 64 in the first rotation 66 correspond in projection angles with the sets of low kVp measurements 62 in the second rotation 68. For example, the set of low kVp measurements 67 corresponds in projections angles with the high kVp measurements 69. The first rotation beginning with a low kVp measurement will end with a low kVp measurement. The second rotation beginning with a high kVp measurement will end with a high kVp measurement to ensure acquiring the same amount of data for low and high kVp measurements corresponding in projections angles.

In this scheme, two rotation measurements will form one rotation of high kVp measurements and one rotation of low kVp measurements. Besides low pitch helical scan mode (e.g., as depicted in FIG. 2), an axial scan mode can be used in conjunction with this scheme. For an axial scan, measurements will be sufficient for reconstruction with minimum image quality impact if there is no motion or contrast changes. The axial scan can be used for gout, kidney stone analysis, bone edema, non-contrast head bleeding/calcification differentiation and head post contrast bleeding detection.

As a dual energy solution for lower-cost scanners (e.g., lower-cost CT imaging systems), temporal resolution may still be limited compared with current higher-cost dual energy solutions which rely on better hardware. However, using this proposed method on low-end CT scanners will be useful for dual energy CTA applications. With low pitch helical scan and the tube kVp switching strategy, there will be a full set of high kVp and low kVp rotation measurements that are sufficient for reconstruction. Although the scan is slower than higher-cost CT, it can achieve normal volume coverage capability for value CT. The decreasing k (kVp switching frequency per rotation) and increasing n (if the views per rotation, m, is kept as system defined constant number) can accommodate faster rotation speed even though the kVp switching capability is limited.

In certain embodiments, if temporal resolution needs to be improved, half-scan reconstruction can also be implemented and a full $4\pi$ range of data is not needed. For example, parallel projections can be acquired via fan beam to parallel beam rebinning using the same kVp projection view at each tube angle. Then a weighted filter backprojection is used to reconstruct images. For each projection ray ($\beta,\gamma$), its conjugate ray is ($\pi+\beta-\gamma,-\gamma$) or ($3\pi+\beta-\gamma, -\gamma$). If projection ray ($\beta,\gamma$) is a high kVp measurement, one of the conjugate rays will be high kVp measurements. A weighting scheme can also be implemented to further improve the temporal performance. The weighting function can be determined by the cone angle to the reconstruction plane of the projection rays. The larger the cone angle, the smaller the weights.

In one embodiment, in Equation 1, when k=0, it becomes the rotate-rotate mode, in which the CT scanner measures a first energy signal (e.g., high kVp signal) at one rotation and measures a second energy signal (e.g., low kVp signal) at another rotation. This method works best for axial mode due to less motion and no contrast. It should be pointed out that we can also do half-scan at one kVp and another half-scan at another kVp. Then half-scan based reconstruction can be used to generate images. This will work for both axial and helical scan modes.

There is one kVp switching mode which does not satisfy Equation 1 but still can be considered as a good candidate for providing dual energy imaging. We can use a half-scan switching acquisition where kVp only switches once approximately every 220 to 240 degrees (>half-scan+fan angle). Half-scan based reconstruction is used here to generate high and low kVp images. This mode works for both axial and low pitch helical acquisitions.

Figure 3:
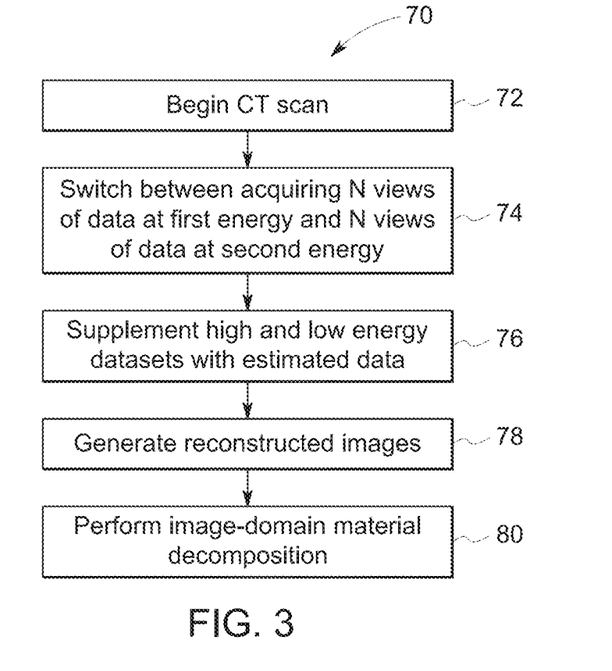
FIG. 3 is a flow diagram of an embodiment of a method for performing kVp switching for dual energy imaging (e.g., utilizing image-domain material decomposition), in accordance with aspects of the present disclosure.

FIG. 3 is a flow diagram of an embodiment of a method 70 for performing kVp switching for dual energy imaging (e.g., utilizing image-domain material decomposition). One or more steps of the method 70 may be performed by components of the CT imaging system 10 in FIG. 1 (e.g., processing circuitry and memory). The method 70 includes beginning a CT imaging scan (block 72). The imaging scan may utilize either two half-scans (e.g., when utilizing half-scan reconstruction) or two full-scans (e.g., two full rotations).

The method 70 also include acquiring a first dataset of projection measurements at a first energy spectrum (e.g., low kVp) and a second dataset of projection measurements at a second energy spectrum (e.g., high kVp) different from the first energy spectrum by switching between acquiring the first dataset for a set number of consecutive views (e.g., n views) at different projection angles at the first energy spectrum and acquiring the second dataset for the set number of consecutive views at different projection angles at the second energy spectrum, wherein the set number of consecutive views is greater than one (block 74). The switching between low kVp and high kVp after the set number of consecutive views may occur repeatedly until a desired total number of views (e.g., m views in Equation 1) are acquired for each half-scan or full-scan. When multiple half-scans or full scans are utilized, the first half-scan or full-scan may begin with acquiring projection measurements at the first energy (e.g., low kVp) and the second half-scan or full-scan may begin with acquiring projection measurements at the second energy (e.g., high kVp) or vice versa. The amount of data acquired for both the first dataset and the second dataset are the same. In addition, the projection angles for the low kVp projection in the first half-scan or full-scan correspond to the projection angles for the high kVp projection in the second half-scan or full-scan. Similarly, the projection angles for the high kVp projection in the first half-scan or full-scan correspond to the projection angles for the low kVp projection in the second half-scan or full-scan. The first half-scan or full-scan beginning with a low kVp measurement will end with a low kVp measurement. The second half-scan or full-scan beginning with a high kVp measurement will end with a high kVp measurement to ensure acquiring the same amount of data for low and high kVp measurements corresponding in projections angles. In the case of utilizing half-scan reconstruction with the kVp switching, additional data may need to be generated to provide enough data for performing the disclosed techniques. For example, in certain embodiments (when utilizing half-scan reconstruction), additional projection measurements (e.g., parallel projections) may be acquired or generated as described above.

The method 70 further includes supplementing both the first dataset with estimated projection measurements at the first energy spectrum and the second dataset with estimated projection measurements at the second energy spectrum to provide missing projection measurements at different projection angles not acquired during the imaging scan for the first dataset and the second dataset respectively (block 76). The missing projection measurements supplied to the first dataset may be derived from the first dataset, the second dataset or both. Similarly, the missing projection measurements supplied to the second dataset may be derived from the first dataset, the second dataset, or both. In any scenario, the missing projection measurements are derived from the acquired projection measurements.

The estimation of the projection measurements may occur in a couple of ways. In one embodiment, a two-dimensional reconstruction method may be utilized. With this method, at specified reconstruction plane position, a view range of $\pi$ parallel single row projection data set for high kVp or low kVp with tube angle $\beta \in [\beta_0 \ \beta_e]$ can be formed. A missing measurement at projection ray $(\beta, \gamma)$ is estimated from multiple measurements in a low pitch helical scan with weighted average method based on the tube distance to the reconstruction plane. In particular, a missing measurement at $(\beta, \gamma)$, which could be a high kVp measurement or low kVp measurement can be estimated from $(\beta+2\pi, \gamma)$ and $(\beta-2\pi, \gamma)$ measurements. For example, if $(\beta, \gamma)$ is a low kVp measurement and a high kVp measurement needs to be estimated, projection $(\beta+2\pi, \gamma)$ and $(\beta-2\pi, \gamma)$ should be high kVp measurements and can be used to estimate high kVp measurements in a low pitch helical scan with weighted average method based on the tube distance to the reconstruction plane. After a full two-dimensional data set is formed, a filtered backprojection is used to reconstruct high kVp and low kVp images.

In another approach, an algorithm utilizes the two neighboring 27c data (e.g., projection data from the two neighboring rotation 66, 68) to fill in the views. For example, the first high kVp view (e.g., high kVp set 77 in rotation 66 of FIG. 2) from the first 27c span could be trained to be converted to a low kVp view by using the low kVp view (e.g., low kVp set 79 in rotation 68 in FIG. 2) from the second neighboring 27c span acquired at the same tube angle (e.g., projection angle) as a guide. In other words, the low kVp sets 62 in rotation 68 of FIG. 2 may be utilized to fill in the missing projection data between the low kVp sets in rotation 66 and the high kVp sets 64 in rotation 66 of FIG. 2 may be utilized to fill in the missing projection data between the high kVp sets in rotation 68 or vice versa. In certain embodiments, a deep neural network (e.g., convolutional neural network) may be trained and utilized to generate the estimated projection measurements for both the first and second datasets. For example, the deep neural network may be trained to estimate a missing low kVp measurement from a high kVp measurement at the corresponding angle in the adjacent rotation or vice versa. Also, the deep neural network may be trained to estimate a missing low kVp measurement from adjacent high kVp measurements flanking the missing low kVp measurement within the same rotation or vice versa. In certain embodiments, the deep neural network may be trained to utilize flanking measurements at a different energy from the energy of the missing measurement within the same rotation as the missing measurement and measurements at the different energy at the corresponding angle in the adjacent rotation to estimate the missing measurement.

Returning to the method 70, the method 70 includes generating reconstructed images (block 78). In particular, a first energy (e.g., low kVp) reconstructed image and a second energy (e.g., high kVp) reconstructed image are generated from the supplemented first and second datasets, respectively. The method 70 also includes performing image-domain material decomposition on the first and second energy reconstructed images to generate material images (e.g., material decomposition images or basis material images) that may be utilized for various dual imaging applications (block 80).

Figure 4:
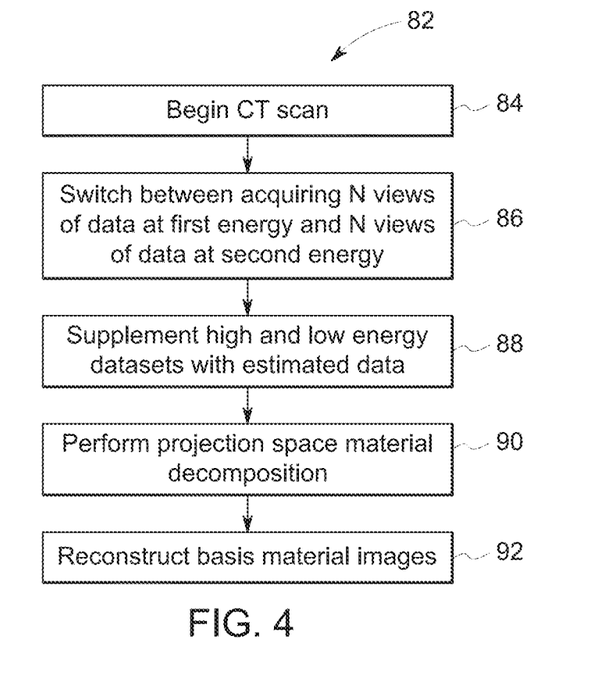
FIG. 4 is a flow diagram of an embodiment of a method for performing kVp switching for dual energy imaging (e.g., utilizing projection space material decomposition), in accordance with aspects of the present disclosure.

FIG. 4 is a flow diagram of an embodiment of a method 82 for performing kVp switching for dual energy imaging (e.g., utilizing projection space material decomposition). One or more steps of the method 70 may be performed by components of the CT imaging system 10 in FIG. 1 (e.g., processing circuitry and memory). Blocks 84, 86, and 88 in the method 82 are the same as blocks 72, 74, and 76 in the method 70.

The method 84 includes performing projection space material decomposition on the supplemented first and second datasets to generate basis material projections (block 90). The method 84 also includes reconstructing material images (e.g., material decomposition images or basis material images) from the basis material projections that may be utilized for various dual energy imaging applications (block 92).

Figure 5:
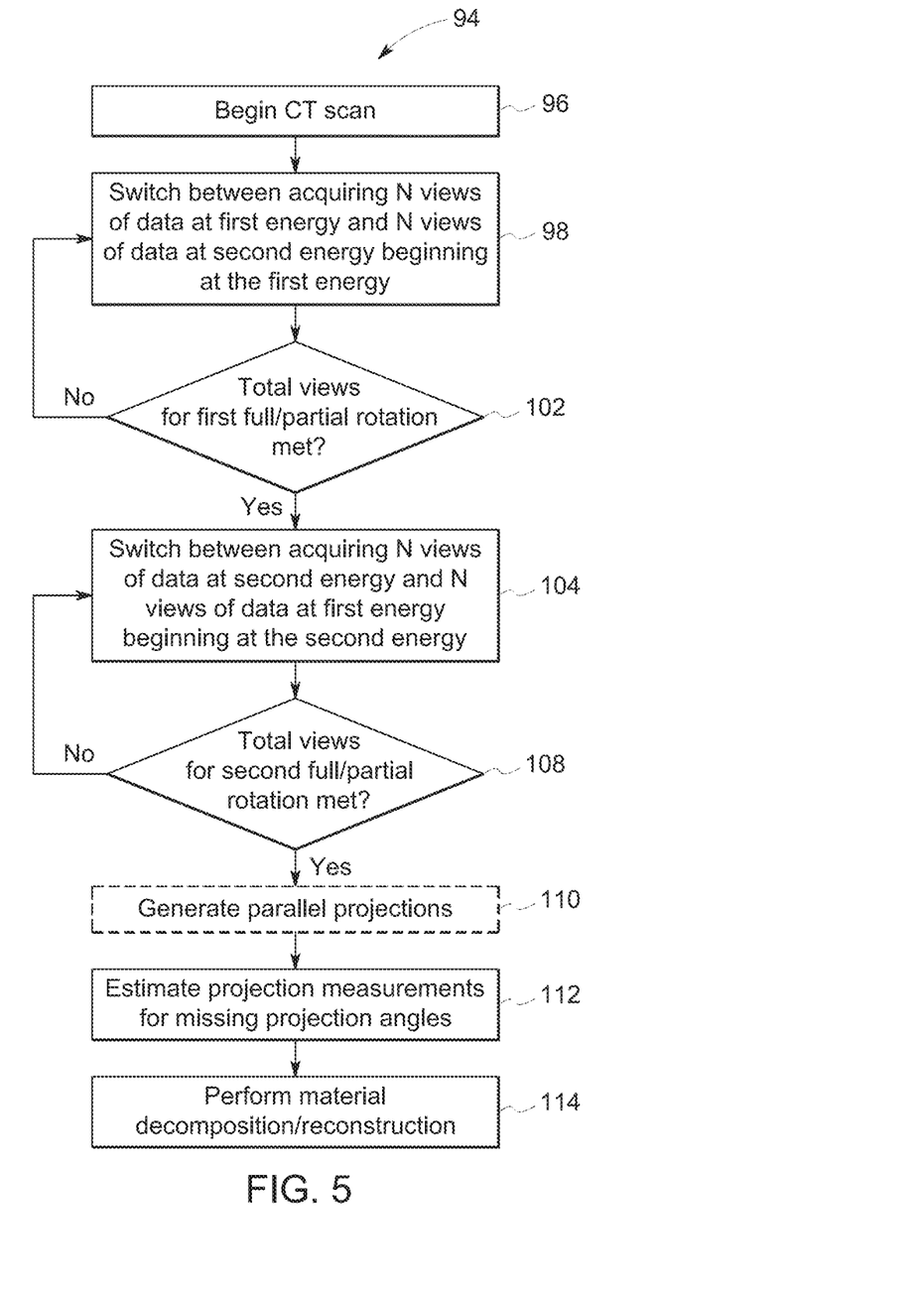
FIG. 5 is a flow diagram of an embodiment of a method for performing kVp switching for dual energy imaging, in accordance with aspects of the present disclosure.

FIG. 5 is a flow diagram of an embodiment of a method 94 for performing kVp switching for dual energy imaging. One or more steps of the method 94 may be performed by components of the CT imaging system 10 in FIG. 1 (e.g., processing circuitry and memory). The method 70 includes beginning a CT imaging scan (block 96). The imaging scan may utilize either two half-scans (e.g., when utilizing half-scan reconstruction) or two full-scans (e.g., two full rotations). In certain embodiments, the number of rotations may be different (e.g., 4 rotations, 6 rotations, etc.).

The method 94 also includes switching between acquiring a first dataset of projection measurements at a first energy spectrum (e.g., low kVp) for a set number of views (e.g., n views in Equation 1, where n is greater than 1) at different projection angles during the first full or partial rotation and acquiring a second dataset of projection measurements at a second energy spectrum (e.g., high kVp) different from the first energy spectrum for the same set number of views at different projection angles during the first full or partial rotation (block 98). The method 94 then determines if the total number of views (e.g., m views in Equation 1) for the first full or partial rotation are met (block 102). If the total number of views for the first full or partial rotation are not met, the method 94 repeats blocks 98, 100, and 102. It should be noted the first full or partial rotation begins and ends with acquiring projection measurements at the first energy spectrum. If the total number of view for the first full or partial rotation or met, the method 94 includes switching between acquiring the second dataset of projection measurements at the second energy spectrum (e.g., high kVp) for the same set number of views at different projection angles during the second full or partial rotation and acquiring the first dataset of projection measurements at the first energy spectrum (e.g., low kVp) for the same set number of views at different projection angles during the second full or partial rotation (block 104). The method 94 then determines if the total number of views (e.g., m views in Equation 1) for the second full or partial rotation are met (block 102). If the total number of views for the second full or partial rotation are not met, the method 94 repeats blocks 104, 106, and 108. It should be noted the second full or partial rotation begins and ends with acquiring projection measurements at the second energy spectrum. After block 108, the amount of data acquired for both the first dataset and the second dataset are the same. In addition, the projection angles for the low kVp projection in the first half-scan or full-scan correspond to the projection angles for the high kVp projection in the second half-scan or full-scan. Similarly, the projection angles for the high kVp projection in the first half-scan or full-scan correspond to the projection angles for the low kVp projection in the second half-scan or full-scan.

If the total number of view for the second full or partial rotation or met, the method 94 moves on. In certain embodiments utilizing half-scan reconstruction with the kVp switching, the method 94 includes generating additional data (e.g., parallel projections) to provide enough data for performing the disclosed techniques as described above (block 110).

The method 94 also includes estimating projection measurements for missing projection angles not acquired during the imaging scan to supplement both the first dataset at the first energy and the second dataset at the second energy (block 112). The missing projection measurements supplied to the first dataset may be derived from the first dataset, the second dataset or both. Similarly, the missing projection measurements supplied to the second dataset may be derived from the first dataset, the second dataset, or both. In any scenario, the missing projection measurements are derived from the acquired projection measurements. The estimation of the projection measurements may occur as described in FIG. 3.

The method 94 further includes performing material decomposition and reconstruction to generate material images (e.g., material decomposition images or basis material images) (block 114). In certain embodiments, projection space material decomposition is performed on the supplemented first and second datasets to generate basis material projections, followed by reconstructing material images from the basis material projections. In certain embodiments, image-space decomposition is performed on the supplemented first and second datasets to generate a reconstructed image at the first energy and a reconstructed image at the second energy, respectively, followed by image-domain material decomposition to generate material images.

Technical effects of the disclosed subject matter include enable the utilization of kVp switching technology for dual energy imaging on low-end CT imaging systems (which lack typical hardware solutions for dual energy imaging) that consist of cost effective hardware and only have lower kVp switching capability. The utilization of kVp switching technology for dual energy imaging applications may occur solely via a software update (i.e., without any hardware changes). Thus, low-end CT imaging systems may use dual energy for a vast number of clinical applications (e.g., kidney stones, lesion characterization, bone edema, etc.).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A computer-implemented method, comprising:
acquiring, during an imaging scan, a first dataset of projection measurements at a first energy spectrum and a second dataset of projection measurements at a second energy spectrum different from the first energy spectrum by switching between acquiring the first dataset for a set number of consecutive views at different projection angles at the first energy spectrum and acquiring the second dataset for the set number of consecutive views at different projection angles at the second energy spectrum, wherein the set number of consecutive views is greater than one; and supplementing both the first dataset with estimated projection measurements at the first energy spectrum and the second dataset with estimated projection measurements at the second energy spectrum to provide missing projection measurements at different projection angles not acquired during the imaging scan for the first dataset and the second dataset respectively.

2. The computer-implemented method of claim 1, wherein an amount of data acquired for both the first dataset and the second dataset are the same.

3. The computer-implemented method of claim 1, wherein the estimated projection measurements at the first energy spectrum and the second energy spectrum are derived from both the first dataset and the second dataset, and wherein the estimated projection measurements at the first energy spectrum correspond in projection angles with both the first dataset and the second dataset of projection measurements they are derived from and the estimated projection measurements at the second energy spectrum correspond in projection angles with both the first dataset and the second dataset of projection measurements they are derived from.

4. The computer-implemented method of claim 1, comprising:
   after supplementation, separately generating a first reconstructed image from the first dataset and a second reconstructed image from the second dataset; and
   performing image-domain material decomposition on the first reconstructed image and the second reconstructed image to generate basis material images.

5. The computer-implemented method of claim 1, comprising:
   after supplementation, performing projection space material decomposition on the first dataset and the second dataset to generate basis material projections; and
   reconstructing basis material images from the basis material projections.

6. The computer-implemented method of claim 1, wherein switching between acquiring the first dataset for the set number of consecutive views at different projection angles at the first energy spectrum and acquiring the second dataset for the set number of consecutive views at different projection angles at the second energy spectrum occurs repeatedly.

7. The computer-implemented method of claim 6, wherein switching between acquiring the first dataset for the set number of consecutive views at different projection angles at the first energy spectrum and acquiring the second dataset for the set number of consecutive views at different projection angles at the second energy spectrum occurs repeatedly over a first full rotation beginning with acquiring the first dataset and then repeatedly over a second full rotation beginning with acquiring the second dataset.

8. The computer-implemented method of claim 7, wherein the first dataset acquired during the first full rotation corresponds in projection angle with the second dataset acquired during the second full rotation.

9. The computer-implemented method of claim 1, wherein the estimated projection measurements at the first energy spectrum and the second energy spectrum are derived utilizing a trained deep neural network.

10. One or more non-transitory computer-readable media encoding one or more processor-executable routines, wherein the one or more routines, when executed by a processor, cause acts to be performed comprising:

acquiring, during an imaging scan, a first dataset of projection measurements at a first energy spectrum and a second dataset of projection measurements at a second energy spectrum different from the first energy spectrum by switching between acquiring the first dataset for a set number of consecutive views at different projection angles at the first energy spectrum and acquiring the second dataset for the set number of consecutive views at different projection angles at the second energy spectrum, wherein the set number of consecutive views is greater than one; and supplementing both the first dataset with estimated projection measurements at the first energy spectrum and the second dataset with estimated projection measurements at the second energy spectrum to provide missing projection measurements at different projection angles not acquired during the imaging scan for the first dataset and the second dataset respectively.

11. The one or more non-transitory computer-readable media of claim 10, wherein an amount of data acquired for both the first dataset and the second dataset are the same.

12. The one or more non-transitory computer-readable media of claim 10, wherein the estimated projection measurements at the first energy spectrum and the second energy spectrum are derived from both the first dataset and the second dataset, and wherein the estimated projection measurements at the first energy spectrum correspond in projection angles with both the first dataset and the second dataset of projection measurements they are derived from and the estimated projection measurements at the second energy spectrum correspond in projection angles with both the first dataset and the second dataset of projection measurements they are derived from.

13. The one or more non-transitory computer-readable media of claim 10, wherein switching between acquiring the first dataset for the set number of consecutive views at different projection angles at the first energy spectrum and acquiring the second dataset for the set number of consecutive views at different projection angles at the second energy spectrum occurs repeatedly.

14. The one or more non-transitory computer-readable media of claim 13, wherein switching between acquiring the first dataset for the set number of consecutive views at different projection angles at the first energy spectrum and acquiring the second dataset for the set number of consecutive views at different projection angles at the second energy spectrum occurs repeatedly over a first full rotation beginning with acquiring the first dataset and then repeatedly over a second full rotation beginning with acquiring the second dataset.

15. The one or more non-transitory computer-readable media of claim 14, wherein the first dataset acquired during the first full rotation corresponds in projection angle with the second dataset acquired during the second full rotation.

16. A processor-based system, comprising:
   a memory encoding processor-executable routines; and
   a processor configured to access the memory and to execute the processor-executable routines, wherein the routines, when executed by the processor, cause the processor to:
      acquire, during an imaging scan, a first dataset of projection measurements at a first energy spectrum and a second dataset of projection measurements at a second energy spectrum different from the first energy spectrum by switching between acquiring the first dataset for a set number of consecutive views at different projection angles at the first energy spectrum and acquiring the second dataset for the set number of consecutive views at different projection angles at the second energy spectrum, wherein the set number of consecutive views is greater than one; and supplement both the first dataset with estimated projection measurements at the first energy spectrum and the second dataset with estimated projection measurements at the second energy spectrum to provide missing projection measurements at different projection angles not acquired during the imaging scan for the first dataset and the second dataset respectively.

17. The processor-based system of claim 16, wherein an amount of data acquired for both the first dataset and the second dataset are the same.

18. The processor-based system of claim 16, wherein the estimated projection measurements at the first energy spectrum and the second energy spectrum are derived from both the first dataset and the second dataset, and wherein the estimated projection measurements at the first energy spectrum correspond in projection angles with both the first dataset and the second dataset of projection measurements they are derived from and the estimated projection measurements at the second energy spectrum correspond in projection angles with both the first dataset and the second dataset of projection measurements they are derived from.

19. The processor-based system of claim 16, wherein switching between acquiring the first dataset for the set number of consecutive views at different projection angles at the first energy spectrum and acquiring the second dataset for the set number of consecutive views at different projection angles at the second energy spectrum occurs repeatedly.

20. The processor-based system of claim 19, wherein switching between acquiring the first dataset for the set number of consecutive views at different projection angles at the first energy spectrum and acquiring the second dataset for the set number of consecutive views at different projection angles at the second energy spectrum occurs repeatedly over a first full rotation beginning with acquiring the first dataset and then repeatedly over a second full rotation beginning with acquiring the second dataset.

* * * * *